United States Patent
Ansari et al.

(10) Patent No.: US 6,180,577 B1
(45) Date of Patent: Jan. 30, 2001

(54) ANTI-GERM ATTACHMENT—COMPOSITION

(75) Inventors: Shamim Alam Ansari, Princeton; Thomas Gregory Polefka, Somerset, both of NJ (US)

(73) Assignee: Colgate-Palmolive Company, Piscataway, NJ (US)

( * ) Notice: Under 35 U.S.C. 154(b), the term of this patent shall be extended for 0 days.

(21) Appl. No.: 09/304,100

(22) Filed: May 4, 1999

Related U.S. Application Data

(63) Continuation-in-part of application No. 09/226,296, filed on Jan. 7, 1999, now abandoned.
(60) Provisional application No. 60/087,532, filed on Jun. 1, 1998.

(51) Int. Cl.⁷ ..................................................... C11D 1/65
(52) U.S. Cl. ................. 510/132; 510/137; 510/199; 510/387; 510/383; 510/466; 427/70.12; 427/78
(58) Field of Search ..................................... 510/137, 132, 510/199, 382, 383, 466; 424/70.12, 78

(56) References Cited

U.S. PATENT DOCUMENTS

| | | | |
|---|---|---|---|
| 2,698,824 | 1/1955 | Morgulis | 162/90 |
| 2,806,814 | 9/1957 | Richter | 162/93 |
| 5,043,155 | 8/1991 | Puchalski | 424/78 |
| 5,370,876 | 12/1994 | Noll | 422/407 |
| 5,573,709 * | 11/1996 | Wells | 510/122 |
| 5,648,083 | 7/1997 | Blieszner | 424/402 |

FOREIGN PATENT DOCUMENTS

| | | |
|---|---|---|
| 4320401 | 12/1994 | (DE) . |
| 0 378 147 | 7/1990 | (EP) . |
| 0395215 * | 10/1990 | (EP) . |
| 0 395 215 | 10/1990 | (EP) . |
| WO97/16168 | 5/1997 | (WO) . |
| 97/16168 * | 5/1997 | (WO) . |

OTHER PUBLICATIONS

PCT Search Report Dated Oct. 11, 1999.

* cited by examiner

*Primary Examiner*—Kery Fries

(57) ABSTRACT

A method for inhibiting attachment of germs to the skin which comprises applying to the skin a composition comprising:
(a) a skin cleansing effective amount of a surfactant or mixture of surfactants;
(b) a silicone in amounts effective to inhibit attachment of germs to the skin, and rinsing said composition from the skin.

13 Claims, No Drawings

ANTI-GERM ATTACHMENT—COMPOSITION

This is a Continuation-in-Part application of U.S. Ser. No. 9/226,296 filed Jan. 7, 1999, now abandoned, which has priority of provisional application 60/087,532 filed Jun. 1, 1998.

BACKGROUND OF THE INVENTION

Basic skin cleansing compositions have been long addressed by the personal care industry. The consumer population is looking for additional benefit beyond basic skin cleansing which now includes germ as well as soil removal. Recently, intensified focus has been directed to the spread of germs from touching various objects in public use such as an ATM machine, public phones, public restrooms, the gym and the like. New compositions which fight germs have recently been marketed. However, many of these products use high quantities of alcohol to accomplish the degerming of the skin. These products are directed to eliminating pre-existing germs present in the skin prior to treatment. Therefore, a need exists for obtaining a longer lasting "antigerm" effect with a cleansing composition normally employed as a rinse-off product which inhibits the further attachment of germs to the skin following the rinse off process.

Such a product should not be restricted to having activity against only one or a small number of germs which can be present on the skin. It should be readily applicable to a large number of germs, regardless of their gram negative or gram positive nature or whatever type of classification system under which they may be categorized. A few compositions with active agents seem to work by stopping the attachment of specific germs to the skin. However, compositions containing these agents are disclosed to be germ specific to only one or a small number of germs.

It has now been discovered that a relatively simple rinse off skin cleansing composition has the ability to inhibit the attachment of germs to the skin for a significant period of time after rinsing the skin. A broad spectrum of germs can be inhibited. In this manner a standard rinse off skin cleansing composition provides a desired benefit to the everyday skin washing population. Additionally, it can provide a meaningful benefit to those individuals whose skin is in particular need to have diminished levels of germs thereon, for example those people suffering from atopic dermatitis, psoriasis, immunodeficient conditions and the like.

A further advantage of the composition is that germs which are present, can be more readily removed from the skin by rinsing with water after treatment of the skin with the composition of the invention. This occurs for a period of time after the initial rinse-off of the composition has occurred.

SUMMARY OF THE INVENTION

In accordance with the invention, there is a method for inhibiting the attachment of germs to the skin which comprises applying to the skin a composition comprising
  a. a skin cleansing effective amount of a surfactant or mixture of surfactants,
  b. a silicone component in amounts effective to inhibit attachment of germs to the skin, and rinsing said composition from the skin.

A further aspect of the invention is the composition having as an additional component a cationic material, preferably a cationic polymer.

Additionally, a composition which accomplishes the goal of inhibition of germ attachment is the composition of (a) and (b) above.

Still further, there is the use of a composition comprising:
  (a) a skin cleansing effective amount of a surfactant or mixture of surfactants,
  (b) a silicone component in amounts effective to inhibit attachment of germs to the skin, in the preparation of a skin cleansing material which inhibits the attachment of germs to the skin.

The composition can work its effects in many realistic situations. It can reduce the spread of germs from inanimate objects, for example door knobs, phones, water faucets and the like as well as through skin to skin contact, for example the shaking of hands. In summary, the transmission of germs to skin can be reduced by prior contact of skin with the composition of this invention.

DETAILED DESCRIPTION OF THE INVENTION

The term "germ" as used in the specification and claims of this invention means bacteria and viruses, particularly bacteria. Examples of bacteria which are inhibited from attaching to the skin include *staphylococcus aureus, staphylococcus epidermis, corynebacterium minutissium, escherichia coli, salmonella, choleraesuis* and *serratia marcescens*. Examples of viruses include human rhinovirus and human rotovirus.

The surfactants which can be used in the composition include the following families: anionic, amphoteric, nonionic and cationic, alone or in combination. Soap a long chain alkyl or alkenyl, branched or normal carboxylic acid salt such as sodium, potassium, ammonium or substituted ammonium salt, can be present in the composition. Exemplary of long chain alkyl or alkenyl are from about 8 to about 22 carbon atoms in length, specifically about 10 to about 20 carbon atoms in length, more specifically alkyl and most specifically normal, or normal with little branching. Small quantities of olefinic bond(s) may be present in the predominantly alkyl sections, particularly if the source of the "alkyl" group is obtained from a natural product such as tallow, coconut oil and the like.

Examples of anionic surfactants other than soap include but are not limited to alkyl sulfates, anionic acyl sarcosinates, methyl acyl taurates, N-acyl glutamates, acyl isethionates, alkyl sulfosuccinates, alkyl phosphate esters, ethoxylated alkyl phosphate esters, trideceth sulfates, protein condensates, mixtures of ethoxylated alkyl sulfates and the like.

Other surfactants can be present in the composition as well. Examples of such surfactants are the anionic, amphoteric, nonionic and cationic surfactants. Examples of anionic surfactants include but are not limited to alkyl sulfates, anionic acyl sarcosinates, methyl acyl taurates, N-acyl glutamates, acyl isethionates, alkyl sulfosuccinates, alkyl phosphate esters, ethoxylated alkyl phosphate esters, trideceth sulfates, protein condensates, mixtures of ethoxylated alkyl sulfates and the like.

Alkyl chains for these surfactants are $C_8$–$C_{22}$, preferably $C_{10}$–$C_{18}$, more preferably $C_{12}$–$C_{14}$. Anionic nonsoap surfactants can be exemplified by the alkali metal salts of organic sulfate having in their molecular structure an alkyl radical containing from about 8 to about 22 carbon atoms and a sulfonic acid or sulfuric acid ester radical (included in the term alkyl is the alkyl portion of higher acyl radicals). Preferred are the sodium, ammonium, potassium or triethanolamine alkyl sulfates, especially those obtained by sulfating the higher alcohols ($C_8$–$C_{18}$ carbon atoms), sodium coconut oil fatty acid monoglyceride sulfates and sulfonates; sodium or potassium salts of sulfuric acid esters of the reaction product of 1 mole of a higher fatty alcohol e.g., tallow or coconut oil alcohols) and 1 to 12 moles of ethylene oxide; sodium or potassium salts of alkyl phenol ethylene oxide ether sulfate with 1 to 10 units of ethylene oxide per molecule and in which the alkyl radicals contain from 8 to 12 carbon atoms, sodium alkyl glyceryl ether sulfonates; the reaction product of fatty acids having from 10 to 22 carbon atoms esterified with isethionic acid and neutralized with sodium hydroxide; water soluble salts of condensation products of fatty acids with sarcosine; and others known in the art.

Zwitterionic surfactants can be exemplified by those which can be broadly described as derivatives of aliphatic quaternary ammonium, phosphonium, and sulfonium compounds, in which the aliphatic radicals can be straight chain or branched and wherein one of the aliphatic substituents contains from about 8 to 18 carbon atoms and one contains an anionic water-solubilizing group, e.g., carboxy, sulfonate, sulfate, phosphate, or phosphonate. A general formula for these compounds is:

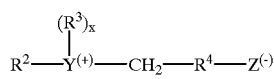

wherein $R^2$ contains an alkyl, alkenyl, or hydroxy alkyl radical of from about 8 to about 18 carbon atoms, from 0 to about 10 ethylene oxide moieties and from 0 to I glyceryl moiety; Y is selected from the group consisting of nitrogen, phosphorus, and sulfur atoms; $R^3$ is an alkyl or monohydroxyalkyl group containing 1 to about 3 carbon atoms; X is I when Y is a sulfur atom and 2 when Y is a nitrogen or phosphorus atom, $R^4$ is an alkylene or hydroxyalkylene of from 0 to about 4 carbon atoms and Z is a radical selected from the group consisting of carboxylate, sulfonate, sulfate, phosphonate, and phosphate groups.

Examples include: 4-[N,N-di(2-hydroxyethyl)-N-octadecylammonio]-butane-1-carboxylate; 5-[S-3-hydroxypropyl-S-hexadecylsulfonio]-3 hydroxypentane-1-sulfate; 3-[P,P-P-diethyl-P 3,6,9 trioxatetradecylphosphonio]-2-hydroxypropane-1-phosphate; 3-[N,N-dipropyl-N-3 dodecoxy-2-hydroxypropylammonio]-propane-1-phosphonate; 3-(N,N-di- methyl-N-hexadecylammonio) propane-1-sulfonate; 3-(N,N-dimethyl-N-hexadecylammonio)-2-hydroxypropane-1-sulfonate; 4-(N,N-di(2-hydroxyethyl)-N-(2-hydroxydodecyl) ammonio]-butane-1-carboxylate; 3-[S-ethyl-S-(3-dodecoxy-2-hydroxypropyl)sulfonio]-propane-1-phosphate; 3-(P,P-dimethyl-P-dodecylphosphonio)-propane-1-phosphonate; and 5-[N,N-di(3-hydroxypropyl)-N-hexadecylammonio]-2-hydroxy-pentane-1-sulfate.

Examples of amphoteric surfactants which can be used in the compositions of the present invention are those which can be broadly described as derivatives of aliphatic secondary and tertiary amines in which the aliphatic radical can be straight chain or branched and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecylaminopropionate, sodium 3-dodecylaminopropane sulfonate, N-alkyltaurines, such as the one prepared by reacting dodecylamine with sodium isethionate according to the teaching of U.S. Pat. No. 2,658,072, N-higher alkyl aspartic acids, such as those produced according to the teaching of U.S. Pat. No. 2,438,091 and U.S. Pat. No. 2,528,378. Other amphoterics such as betaines are also useful in the present composition.

Examples of betaines useful herein include the high alkyl betaines such as coco dimethyl carboxymethyl betaine, lauryl dimethyl carboxy-methyl betaine, lauryl dimethyl alpha-carboxyethyl betaine, cetyl dimethyl carboxymethyl betaine, lauryl bis-(2-hydroxyethyl)carboxy methyl betaine, stearyl bis-(2-hydroxypropyl) carboxymethyl betaine, oleyl dimethyl gamma-carboxypropyl betaine, lauryl bis-(2-hydro-xypropyl) alpha-carboxyethyl betaine, etc. The sulfobetaines may be represented by coco dimethyl sulfopropyl betaine, stearyl dimethyl sulfopropyl betaine, amido betaines, amidosulfobetaines, and the like.

Many cationic surfactants are known to the art. By way of example, the following may be mentioned:

stearyldimenthylbenzyl ammonium chloride;
dodecyltrimethylammonium chloride;
nonylbenzylethyldimethyl ammonium nitrate;
tetradecylpyridinium bromide;
laurylpyridinium chloride;
cetylpyridinium chloride
laurylpyridinium chloride;
laurylisoquinolium bromide;
ditallow(Hydrogenated)dimethyl ammonium chloride;
dilauryldimethyl ammonium chloride; and
stearalkonium chloride.

Additional cationic surfactants are disclosed in U.S. Pat. No. 4,303,543 see column 4, lines 58 and column 5, lines 1–42, incorporated herein by references. Also see CTFA Cosmetic Ingredient Dictionary, 4th Edition 1991, pages 509–514 for various long chain alkyl cationic surfactants; incorporated herein by references.

Nonionic surfactants can be broadly defined as compounds produced by the condensation of alkylene oxide groups (hydrophilic in nature) with an organic hydrophobic compound, which may be aliphatic or alkyl aromatic in nature. Examples of preferred classes of nonionic surfactants are:

1. The polyethylene oxide condensates of alkyl phenols, e.g., the condensation products of alkyl phenols having an alkyl group containing from about 6 to 12 carbon atoms in either a straight chain or branched chain configuration, with ethylene oxide, the said ethylene oxide being present in amounts equal to 10 to 60 moles of ethylene oxide per mole of alkyl phenol. The alkyl substituent in such compounds may be derived from polymerized propylene, diisobutylene, octane, or nonane, for example.

2. Those derived from the condensation of ethylene oxide with the product resulting from the reaction of propylene oxide and ethylene diamine products which may be varied in composition depending upon the balance between the hydrophobic and hydrophilic elements which is desired. For example, compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said base having a molecular weight of the order of 2,500 to 3,000, are satisfactory.

3. The condensation product of aliphatic alcohols having from 8 to 18 carbon atoms, in either straight chain or branched chain configuration with ethylene oxide, e.g., a coconut alcohol ethylene oxide condensate having from 10 to 30 moles of ethylene oxide per mole of coconut alcohol, the coconut alcohol fraction having from 10 to 14 carbon atoms. Other ethylene oxide condensation products are ethoxylated fatty acid esters of polyhydric alcohols (e.g., Tween 20-polyoxyethylene (20) sorbitan monolaurate). 4. Long chain tertiary amine oxides corresponding to the following general formula:

wherein $R_1$ contains an alkyl, alkenyl or monohydroxy alkyl radical of from about 8 to about 18 carbon atoms, from 0 to about 10 ethylene oxide moieties, and from 0 to 1 glyceryl moiety, and, $R_2$ and $R_3$ contain from 1 to about 3 carbon atoms and from 0 to about 1 hydroxy group, e.g., methyl, ethyl, propyl, hydroxy ethyl, or hydroxy propyl radicals. The arrow in the formula is a conventional representation of a semipolar bond. Examples of amine oxides suitable for use in this invention include dimethyldodecylamine oxide, oleyl-di(2-hydroxyethyl) amine oxide, dimethyloctylamine oxide, dimethyldecylamine oxide, dimethyltetradecylamine oxide, 3,6,9 trioxaheptadecyldiethylamine oxide, di(2-hydroxyethyl)-tetradecylamine oxide, 2-dodecoxyethyldimethylamine oxide, 3-dodecoxy-2-hydroxypropyldi(3-hydroxypropyl)amine oxide, dimethylhexadecylamine oxide.

5. Long chain tertiary phosphine oxides corresponding to the following general formula:

wherein R contains an alkyl, alkenyl or monohydroxyalkyl radical ranging from 8 to 20 carbon atoms in chain length, from 0 to about 10 ethylene oxide moieties and from 0 to 1 glyceryl moiety and R' and R" are each alkyl or monohydroxyalkyl groups containing from 1 to 3 carbon atoms. The arrow in the formula is a conventional representation of a semipolar bond. Examples of suitable phosphine oxides are: dodecyldimethylphosphine oxide, tetradecylmethylethylphosphine oxide, 3,6,9-trioxaoctadecyldimethylphosphine oxide, cetyldimethylphosphine oxide, 3-dodecoxy-2-hydroxypropyldi(2-hydroxyethyl) phosphine oxide stearyldimethylphosphine oxide, cetylethyl propylphosphine oxide, oleyldiethylphosphine oxide, dodecyldiethylphosphine oxide, tetradecyldiethylphosphine oxide, dodecyldipropylphosphine oxide, dodecyldi(hydroxymethyl) phosphine oxide, dodecyldi(2-hydroxyethyl)phosphine oxide, tetradecylmethyl-2-hydroxypropylphosphine oxide, oleyldimethylphosphine oxide, 2-hydroxydodecyldimethylphosphine oxide.

6. Long chain dialkyl sulfoxides containing one short chain alkyl or hydroxy alkyl radical of 1 to about 3 carbon atoms (usually methyl) and one long hydrophobic chain which contain alkyl, alkenyl, hydroxy alkyl, or keto alkyl radicals containing from about 8 to about 20 carbon atoms, from 0 to about 10 ethylene oxide moieties and from 0 to 1 glyceryl moiety. Examples include: octadecyl methyl sulfoxide, 2-ketotridecyl methyl sulfoxide, 3,6,9-trioxaoctadecyl 2-hydroxyethyl sulfoxide, dodecyl methyl sulfoxide, oleyl 3-hydroxypropyl sulfoxide, tetradecyl methyl sulfoxide, 3 methoxytridecylmethyl sulfoxide, 3-hydroxytridecyl methyl sulfoxide, 3-hydroxy-4-dodecoxybutyl methyl sulfoxide.

7. Alkylated polyglycosides wherein the alkyl group is from about 8 to about 20 carbon atoms, preferably about 10 to about 18 carbon atoms and the degree of polymerization of the glycoside is from about 1 to about 3, preferably about 1.3 to about 2.0.

Also present in the composition is a silicone. Silicone as used herein is preferably a silicone fluid, as opposed to a silicone gum. A silicone fluid is defined herein as silicone with viscosities ranging from about 5 to about 600,000 centistokes, more preferably from about 350 to about 100,000 centistoke at 25° C. Polyalkyl siloxanes such as polydimethyl siloxane generally known as "dimethicone", are preferred for use as the silicone.

The silicone materials useful in the present invention are generally non-volatile and may be either a polyalkyl siloxane, a polyaryl siloxane, a polyalkylaryl, a functionalized siloxanelated, a polysiloxane such as a polysiloxan with amino functional substitution, an alkoxylated silicone, such as ethoxylated or propoxylated, and a polyether siloxane copolymer. The silicones useful in the present invention may be endcapped with any number of moieties, including, for example, methyl, hydroxyl, ethylene oxide, propylene oxide, amino, trialkyl silane (preferably methyl), carboxyl, and the like. Mixtures of these materials may also be used and are preferred in certain implementations. Additionally, volatile silicones may be used as part of the silicone mixture so long as the final mixture is at least essentially non-volatile.

The polyalkyl silicones that may be used herein include, for example, polydimethyl siloxanes with viscosities ranging from about 5 to about 600,000 centistokes at 25° C. These siloxanes are available, for example, from General Electric Company as the Viscasil series and from Dow Corning as the Dow Corning 200 series. The viscosity can be measured by means of a glass capillary viscometer as set forth in Dow Corning Corporate Test Method CTM0004, Jul. 20, 1970. Preferably the viscosity ranges from about 50 centistokes to about 150,000 centistokes and most preferably from about 350 centistokes to about 100,000 centistokes.

The polyalkylaryl silicones that may be used include, for example, polymethylphenylsiloxanes having viscosities of from about 15 to about 65 centistokes at 25° C. These siloxanes are available, for example, from the General Electric Company as SF 1075 methyl phenyl fluid or from Dow Corning as 556 Cosmetic Grade Fluid. Additionally, poly(dimethyl siloxane) (diphenyl siloxane) copolymers having a viscosity in the range of from about 10 to about 100,000 centistokes at 25° C. are useful. The polyether siloxane copolymer that may be used is, for example, a polypropylene oxide modified dimethylpolysiloxane (e.g., Dow Corning DC-1248, although ethylene oxide or mixtures of ethylene oxide and propylene oxide may also be used.

References disclosing suitable silicones include U.S. Pat. No. 2,826,551, issued Mar. 11, 1958; Green; U.S. Pat. No. 3,964,500, issued Jun. 22, 1967, Drakoff; U.S. Pat. No. 4,364,837, issued Dec. 21, 1982, Pader; and British Patent No. 849,433, Wooston, published Sep. 28, 1960. All of these patents are incorporated herein by reference. Also incorporated herein by reference is Silicon Compounds, distributed by Petrarch Systems, Inc., 1984. This reference provides a good listing of suitable silicone material.

Although not essential, the presence of a cationic polymer in the composition is preferred.

Cationic polymers includes but are not limited to the following groups:

(i) cationic polysaccharides;

(ii) cationic copolymers of saccharides and synthetic cationic monomers, and (iii) synthetic polymers selected from the group consisting of:

a. cationic polyalkylene imines
b. cationic ethoxy polyalkylene imines
c. cationic poly[N-[3-(dimethylammonio)propyl] N'[3-(ethyleneoxyethylene dimethylammonio)propyl]urea dichloride]
d. in general a polymer having a quaternary ammonium or substituted ammonium ion.

The cationic polysaccharide class encompasses those polymers based on 5 or 6 carbon sugars and derivatives which have been made cationic by engrafting of cationic moieties onto the polysaccharide backbone. They may be composed of one type of sugar or of more than one type, i.e. copolymers of the above derivatives and cationic materials. The monomers may be in straight chain or branched chain geometric arrangements. Cationic polysaccharide polymers include the following: cationic celluloses and hydroxyethylcelluloses; cationic starches and hydroxyalkyl starches; cationic polymers based on arabinose monomers such as those which could be derived from arabinose vegetable gums; cationic polymers derived from xylose polymers found in materials such as wood, straw, cottonseed hulls, and corn cobs; cationic polymers derived from fucose polymers found as a component of cell walls in seaweed; cationic polymers derived from fructose polymers such as Inulin found in certain plants; cationic polymers based on acid containing sugars such as galacturonic acid and glucuronic acid; cationic polymers based on amine sugars such as galactosamine and glucosamine; cationic polymers based on 5 and 6 membered ring polyalcohols; cationic polymers based on galactose monomers which occur in plant gums and mucilages; cationic polymers based on mannose monomers such as those found in plants, yeasts, and red algae; cationic polymers based on galactommannan copolymer known as guar gum obtained from the endosperm of the guar bean.

Specific examples of members of the cationic polysaccharide class include the cationic hydroxyethyl cellulose JR 400 made by Union Carbide Corporation; the cationic starches Stalok® 100, 200, 300, and 400 made by Staley, Inc.; the cationic galactomannans based on guar gum of the Galactasol 800 series by Henkel, Inc. and the Jaguar Series by Celanese Corporation.

The cationic copolymers of saccharides and synthetic cationic monomers useful in the present invention encompass those containing the following saccharides: glucose, galactose, mannose, arabinose, xylose, fucose, fructose, glucosamine, galactosamine, glucuronic acid, galacturonic acid, and 5 or 6 membered ring polyalcohols. Also included are hydroxymethyl, hydroxyethyl and hydroxypropyl derivatives of the above sugars. When saccharides are bonded to each other in the copolymers, they may be bonded via any of several arrangements, such as 1,4-α; 1,4-β; 1,3α; 1,3; 1,3β; and 1,6 linkages. The synthetic cationic monomers for use in these copolymers can include dimethyidiallylammonium chloride, dimethylaminoethyhnethyacrylate, diethyidiallylammonium chloride, N,N-diallyl,N-N-dialklyl ammonium halides, and the like. A preferred cationic polymer is Polyquaternium 7 prepared with drimethyidialkylammonium chloride and acrylamide.

Examples of members of the class of copolymers of saccharides and synthetic cationic monomers include those composed of cellulose derivatives (e.g. hydroxyethyl cellulose) and N,N-diallyl,N-N-dialkyl ammonium chloride available from National Starch Corporation under the tradename Celquat.

Further cationic synthetic polymers useful in the present invention are cationic polyalkylene imines, ethoxypolyalkylene imines, and poly{N[3-(dimethylammonio)-propyl]-N'-[3-(ethyleneoxyethylene dimethylammoniumo) propyl]urea dichloride] CAS Reg. No. 68555-336-2. Preferred cationic polymeric skin conditioning agents of the present invention are those cationic polysaccharides of the cationic guar gum class with molecular weights of 1,000 to 3,000,000. More preferred molecular weights are from 2,500 to 350,000. These polymers have a polysaccharide backbone comprised of galactomannan units and a degree of cationic substitution ranging from about 0.04 per anydroglucose unit to about 0.80 per anydroglucose unit with the substituent cationic group being the adduct of 2,3-epoxypropyl-trimethyl ammonium chloride to the natural polysaccharide backbone. Examples are JAGUAR C-14-S, C-15 and C-17 sold by Celanese Corporation, which trade literature reports have 1% viscosities of from 125 cps to about 3500±500 cps.

Still further examples of cationic polymers include the polymerized materials such as certain quaternary ammonium salts, copolymers of various materials such as hydroxyethyl cellulose and dialkyidimethyl ammonium chloride, acrylamide and beta methacryloxyethyl trimethyl ammonium methosulfate, the quaternary ammonium salt of methyl and stearyl dimethylaminoethyl methacrylate quaternized with dimethyl sulfate, quaternary ammonium polymer formed by the reaction of diethyl sulfate, a copolymer of vinylpyrrolidone and dimethyl aminoethylmethacrylate, quaternized guars and guar gums and the like. Exemplary of cationic polymers which can be used to make the complexes of this invention include, as disclosed in the CTFA International Cosmetic Ingredient Dictionary (Fourth Edition, 1991, pages 461–464); Polyquaternium -1, -2, -4 (a copolymer of hydroxyethylcellulose and diallyidimethyl ammonium chloride), -5 (the copolymer of acrylamide and beta methacrylyloxyethyl trimethyl ammonium methosulfate), -6 (a polymer of dimethyl diallyl ammonium chloride), -7 (the polymeric quaternary ammonium salt of acrylamide and dimethyl diallyl ammonium chloride monomers, -8 (the polymeric 5 quaternary ammonium salt of methyl and stearyl dimethylaminoethyl methacrylate quaternized with dimethyl sulfate), -9 (the polymeric quaternary ammonium salt of polydimethylaminoethyl methacrylate quaternized with methyl bromide), -10 (a polymeric quaternary ammonium salt of hydroxyethyl cellulose reacted with a trimethyl ammonium substituted epoxide), -11 (a quaternary ammonium polymer formed by the reaction of diethyl sulfate and a copolymer of vinyl pyrrolidone and dimethyl aminoethylmethacrylate), -12 (a polymeric quaternary ammonium salt prepared by the reaction of ethyl methacrylate/abietyl methacrylate/diethylaminoethyl methacrylate copolymer with dimethyl sulfate), -13 (a polymeric quaternary ammonium salt prepared by the reaction of ethyl methacrylate/oleyl methacrylate/diethylaminoethyl methacrylate copolymer with dimethyl sulfate), -14, -15 (the copolymer of acrylamide and betamethacrylyloxyethyl trimethyl ammonium chloride), -16 (a polymeric quaternary ammonium salt formed from methylvinylimidazolium chloride and vinylpyrrolidone), -17, -18, -19 (polymeric quaternary ammonium salt prepared by the reaction of polyvinyl alcohol with 2,3 epcxy-propylamine), -20 (the polymeric quaternary ammonium salt prepared by the reaction of polyvinyl octadecyl ether with 2,3-epoxypropylamine), -22, -24 a polymeric quaternary ammonium salt of hydroxyethyl cellulose reacted with a lauryl dimethyl ammonium substituted epoxide), -27 (the block copolymer formed by the reaction of Polyquaternium-2 (q.v.) with Polyquatemium-17 (q.v.)), -28, -29 (is Chitosan (q.v.) that has been reacted with propylene oxide and quaternized with epichlorohydrin), and -30.

An additional component which can be present but need not be present at all is a hydrocarbonaceous material such as a wax, petrolatum, mineral oil, beeswax, a "permethyl" made up of longer chain branched hydrocarbons available from Permethyl Corporation. Permethyls are of the general formula

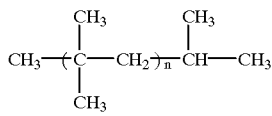

where n can vary from about 4 to over 200. Products where n=4, 16, 38, 214, respectively, are marketed as Permethyl 102A, 104A, 106A and 1082A.

Additional hydrocarbonaceous material which can be employed include lanolins and lanoleic like materials such as long chain alkyl esters and ethers of the lanolins.

The petrolatum useful in the present invention can be any grade of white or yellow petrolatum recognized in the art as suitable for human application. Preferred petrolatum are those with a melting point in a range of from about 35° C. to about 70° C., preferably about 50 to 60° C. The petrolatum of the composition can include hydrocarbon mixtures formulated with mineral oil and/or in combination with paraffin waxes of various melting points; all in small quantities compared to the petrolatum. A petrolatum without additional materials is preferred. Examples of waxes, particularly useful in solid compositions are microcrystalline waxes, generally those waxes which are known as paraffin wax, beeswax, and natural waxes derived from vegetables, shea wax and the like.

Other components can also be present in the composition. These components include preservative(s), colorant(s), UV stabilizer(s), fragrance(s), antibacterial agent(s) and the like. Antibacterial agents include chlorhexidine, Triclosan, triclorcarban and the like at their typically used concentrations, i.e., about 0.1 to about 1.5 wt. %, preferably about 0.15 to about 1.2 wt. % of the composition. When present in the composition(s) of the invention, there is a dual effect. Not only is there an inhibition of germ attachment to the skin following the skin cleansing but there is also the antibacterial effect of the antibacterial agents upon bacteria present on the skin during the skin cleansing.

The preferred surfactant is an anionic surfactant such as soap, alklyisethionate such as sodium cocoylisethionate, a sulfonate, a sulfate (optionally ethoxylated) and the like. Mixtures of surfactants can be employed. There should be sufficient surfactant present to bring about a cleansing effect. The surfactant preferably anionic or mixtures thereof involving one or more from the other families of illustrated surfactants (amphoteric, nonionic and the like) with or without an additional anionic surfactant, can be present in the composition in various quantities. For example broad minimums of the surfactant can be present at 1, 2, 3, 4, 5, 10, 15 or 20 wt. % of the compositions, particularly where the aqueous composition is a liquid. With respect to liquid, preferably aqueous, compositions, the anionic surfactant is from about 2 to about 25 wt. % of the composition, specifically about 5 to about 20 wt. %. Other surfactants may be present such as an amphoteric, particularly a betaine, and a nonionic, particularly an alkylated polyglycoside. Their quantities are from about 1 to about 20 wt. % of the composition. Generally the total surfactant in a liquid composition is at least about 3 or 4 wt. %, preferably at least about 5 wt. % and is generally no more than about 30 wt. %, preferably no more than about 25 wt. % but can be as low as no more than about 10, 15 or 20 wt. %. For a solid composition, the total surfactant can be from about 60 to about 90 wt. %, preferably from about 70 to about 85 wt. %, of the composition. Soap can be present at about 15 to about 100 wt. % of the total surfactant. "Soap-bars" generally have from about 65 to about 90 wt. % soap therein with less than about 10 wt. %, preferably less than about 5 wt. % of other surfactant therein. Most preferably, there is zero or zero to about 2 wt. % of other surfactant therein Bars having a smaller quantity of soap within the disclosed range of soap usually have a mild synthetic surfactant therein such as sodium cocoyl isethionate at moderate to high levels.

The quantity of silicone component is at least about 0.01 wt. %, preferably at least about 0.1 wt. %. of the composition. The maximum can vary but generally is not above about 7 or 8 wt. %., preferably about 5 wt. %, more preferably about 4.5 wt. % of the composition.

When using a cationic polymer in the composition, the quantity of polymer is from about 0.01 to abut 3.0 wt. % of the composition preferably about 0.02 wt. % as a minimum and more preferably about 0.03 wt. % as a minimum. The maximum is generally no more than about 0.9 wt. %, or about 0.75 wt. %, although lower maximums such as about 0.6 wt. % can be employed.

Although not necessary but if present the quantity of hydrocarbonaceous material is at least about 0.1, preferably 0.5 wt. % of the composition. The maximum can vary but generally is not above about 7 or 8 wt. %, preferably a maximum of about 5 wt. % or about 4.5 wt. % of the composition.

The physical nature of the composition is not critical and can be a solid liquid or gel.

The inhibition of germ attachment to the skin is quantitatively assessed by utilizing various bacteria in the protocol below. The ennumerated test bacteria are employed. The number reflects the ATCC catalogue number:

Staph. aureus 6538
Staph. epidermidis 12228
C. minutissimum, 23347
E. coli 11229
Serratia marcescens 14756
Salmonella choleraesuis 10708

The test bacteria are radiolabeled in the following manner:

The test bacteria are grown in log phase in 30 ml of trypticase soy broth (TSB). Next day, bacteria are cetrifuged at 3000 rpm for 20 min at 4° C. The bacterial pellet is resuspended in 20 ml of sterile saline and OD adjusted to 0.1 at 620 nm. Approximately, $10^5$ bacteria (0.1 ml) are inoculated in 5 ml of growth medium (2 ml of Methionine assay medium+3 ml of TSB) for radio-labeling. Fifty microliter of $^{14}C$ methionine (=5 uCi) are added into the tube and incubated overnight at 37° C. in a shaker incubator. Next day, the bacteria are pelleted by centrifuging at 3 K rpm for 15 min at 4° C. This step is repeated for a total of three times to remove free $^{14}C$. Each time 25 $\mu$l of supernatant and 25 $\mu$l of resuspended pellets are collected in scintillation vials for activity measurement. Usually after 3 washes, very little free activity remain in the supernatant.

Control for inoculum-25 $\mu$l of labeled bacteria are transferred into vials in triplicate for input control.

The following soap bars are prepared having approximately 10 wt. % water and 1% of fragrance. The control soap bar of 1% fragrance, 10 wt. % water and the remainder essentially soap is employed. The quantity of soap in the test bars below is reduced by the quantity of silicone employed.

Dimethicone of 1 wt. % from GE has a viscosity of 60,000 centistokes.

Product Preparation

5% solutions of the product are made in deionized water (weigh 5 g and dissolve in 100 ml of deionized water by gentle heating).

Product Application

Soak cotton ball with the product solution and rub on a pig skin piece approximately 2.5 cm obtained from the belly region for 15 sec and lather for 45 sec and finally rinse for 15 sec in running warm (30° C.) tap water.

Bacterial Attachment

Wait till no moisture left on the skin. Apply 25 µl of labeled bacterial suspension all over the skin using a positive displacement pipette. Elute at 2 min after deposition or after 30 min of deposition) with 0.5 ml of letheen broth three times and collect in a scintillation vial.

Control for Inoculum

Transfer 25 µl of labeled bacteria into vials in triplicate for input control.

The results below show the quantity of bacteria left on the skin sample(s) following removal of the bacterial suspension after a contact time of 1–2 minutes or thirty (30) minutes.

TABLE I

| Bacteria | Soap treatment (15 sec. Rubbing, 45 sec. Lathering, 15 sec. Rinsing) | Bacteria remained attached to the skin at 2 min. (%) | | Bacteria remained attached to the skin at 30 min. (%) | |
|---|---|---|---|---|---|
| S. aureus 235,000 | Placebo | 39,420 | (16.9) | 84,941 | (36.2) |
| | Dimethicone 1% | 18,777 | (8.1) | 59,930 | (25.6) |
| S. epiderm 107,506 | Placebo | 24,822 | (23.1) | 30,940 | (28.8) |
| | Dimethicone 1% | 19,222 | (17.9) | 21,294 | (19.8) |
| C. minutis 240,000 | Placebo | 61,950 | (25.7) | 104,895 | (43.6) |
| | Dimethicone 1% | 35,025 | (14.5) | 56,340 | (23.3) |
| E. coli 266,000 | Placebo | 50,508 | (19.0) | 66,544 | (25.0) |
| | Dimethicone 1% | 14,906 | (5.6) | 31,816 | (12.0) |
| S. marcescen 295,000 | Placebo | 31,892 | (10.8) | 61,368 | (20.8) |
| | Dimethicone 1% | 12,760 | (4.3) | 13,888 | (4.7) |
| S. choleraesu 236,000 | Placebo | 12,574 | (9.2) | 13,912 | (10.2) |
| | Dimethicone 1% | 7,096 | (5.2) | 12,232 | (9.0) |

The data clearly shows that the presence of silicone inhibits the attachment of various bacteria to the skin.

As well as the rinse off compositions, the effect of inhibition of germ attachment also occurs with leave on compositions such as creams, lotions, and the like. These latter compositions are characterized by the fact that they are intended to be left on the skin for an extended period of time as opposed to an ordinary cleansing composition which is rinsed off by water after a relatively short contact time with the skin. After rinsing these "leave on" compositions, inhibition of germ attachment to the skin occurs. Desirable is the inhibition of attachment of bacteria to the skin. There need not be a surfactant in cleansing amounts present in the "leave on". Below are exemplary compositions of the "leave on" compositions of the invention.

LOTION

| Ingredient | % |
|---|---|
| Water | 82.91 |
| Dimethylpolysiloxane | 0.5 |
| Magnesium Aluminum Silicate | 0.08 |

LOTION

| Ingredient | % |
|---|---|
| Glycerin | 2.60 |
| Glyceryl/PEG-100 Stearate | 1.60 |
| Sodium Cetearyl Sulphate | 0.32 |
| Cetearyl Alcohol | 0.60 |
| Mineral Oil-Light | 4.00 |
| Dimethicone | 0.80 |
| Petrolatum | 1.00 |
| Tocopheryl Acetate | 0.50 |
| Isopropyl Palmitate | 2.60 |
| Carbomer 2984 | 0.30 |
| Deionized Water | 1.00 |
| 99% Triethanolamine | 0.30 |
| Phenoxyethanol | 0.15 |
| Methyldibromo Glutaronitrile | 0.10 |
| Fragrance | 0.30 |
| Polysorbate 60 | 0.16 |
| Vitamin A Palmitate | 0.08 |
| D Panthenol 50-P | 0.10 |

-continued

LOTION

| Ingredient | % |
|---|---|
| Total | 100.00 |

CREAM

| Ingredient | % |
|---|---|
| Water | 80.60 |
| Dimethylpolysiloxane | 1.00 |
| Magnesium Aluminum Silicate | 0.10 |
| Glycerin | 2.00 |
| Glyceryl Stearate/PEG-100 Stearate | 2.00 |
| Sodium Cetearyl Sulphate | 0.32 |
| Isohexadecane | 1.50 |
| Cetyl-Stearyl Alcohol 50-50 | 0.75 |
| Mineral Oil-Light | 5.00 |
| Dimethicone | 1.00 |
| Petrolatum | 1.25 |
| Tocopheryl Acetate | 0.50 |

-continued

CREAM

| Ingredient | % |
|---|---|
| Isopropyl Palmitate | 2.00 |
| Carbomer 2984 | 0.36 |
| 99% Triethanolamine | 0.36 |
| Fragrance | 0.30 |
| Phenoxyethanol | 0.15 |
| Methyldibromo Glutaronitrile | 0.10 |
| Polysorbate 60 | 0.20 |
| Vitamin A Palmitate | 0.01 |
| D Panthenol 50-P | 0.50 |
| Total | 100.00 |

The liquid compositions of the invention in either rinse off or leave on formulations are desirably oil-in-water emulsions. They, as well as the solid compositions, perform their inhibition of attachment of germs without any topically active drugs or medication present in the compositions, particularly those drugs or medications associated with relieving or minimizing conditions in the target group such as atopic dermatitis, psoriasis, immunodeficient conditions and the like. Examples of such agents include amcinonide, diflorasone diacetate, hydrocortisone and the like for dermatitis; and anthralin, methoxsalen, coal tar and the like for psoriasis. Therefore, such topical agents and medications can be desirably left out completely from all the compositions of this invention or can be present in the composition in amounts which are not sufficient to perform their intended function with respect to the target group, particularly those having atopic dermatitis, psoriasis, immunodeficient conditions and the like.

What is claimed is:

1. A method for inhibiting the attachment of germs to the skin of people having a skin condition selected from the group consisting of atopic dermatitis, psoriasis, or immunodificient condition which comprises applying to the skin a composition having
    (a) a skin cleansing effective amount of a surfactant or mixture of surfactants,
    (b) a silicone in amounts effective to inhibit attachment of germs to the skin, and rinsing with water said composition from the skin.

2. The method in accordance with claim 1 wherein a cationic polymer is also present.

3. The method in accordance with claim 1 wherein a hydrocarbonaceous component is also present.

4. The method in accordance with claim 2 wherein a hydrocarbonaceous component is also present.

5. The method in accordance with claim 1 wherein(b) is from about 0.01 to about 8 wt. % of the composition.

6. The method in accordance with claim 2 wherein the cationic polymer is from about 0.01 to about 3.0 wt. % of the composition.

7. The method in accordance with claim 1 wherein a hydrocarbonaceous component is not present.

8. The method in accordance with claim 1 wherein an antibacterial effective amount of an antibacterial agent is present in the composition.

9. A method for inhibiting the attachment of germs to the skin of people having a skin condition selected from the group consisting of atopic dermatitis, psoriasis, or immunodeficient condition which comprises applying to the skin a composition having
    (a) a skin cleansing effective amount of a surfactant or mixture of surfactants,
    (b) a silicone in amounts effective to inhibit attachment of germs to the skin, and
    (c) a hydrocarbonaceous component in not more than about 8 wt % of the composition, and rinsing said composition from the skin.

10. The method in accordance with claim 9 where a cationic polymer is also present.

11. The method in accordance with claim 10 wherein the cationic polymer is from about 0.01 to about 3.0 wt. % of the composition.

12. The method in accordance with claim 9 wherein an antibacterial effective amount of an antibacterial agent is present in the composition.

13. The method in accordance with claim 9 wherein the composition is rinsed with water from the skin.

* * * * *